(12) United States Patent
Yamashita et al.

(10) Patent No.: US 6,611,698 B1
(45) Date of Patent: Aug. 26, 2003

(54) OPTICAL MEASURING INSTRUMENT

(75) Inventors: Yuichi Yamashita, Kawagoe (JP); Atsushi Maki, Hachioji (JP); Fumio Kawaguchi, Hinode (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/807,478
(22) PCT Filed: Oct. 7, 1999
(86) PCT No.: PCT/JP99/05561
§ 371 (c)(1),
(2), (4) Date: May 24, 2001
(87) PCT Pub. No.: WO00/22415
PCT Pub. Date: Apr. 20, 2000

(30) Foreign Application Priority Data

Oct. 13, 1998 (JP) .......................... 10-290878

(51) Int. Cl.[7] ................................ A61B 5/00
(52) U.S. Cl. ................. 600/310; 600/322; 600/335; 600/473; 600/340
(58) Field of Search ................... 600/310, 322–324, 600/335–336, 407, 473, 476, 340–342, 319–320, 323, 337, 341

(56) References Cited

U.S. PATENT DOCUMENTS

| | | | | |
|---|---|---|---|---|
| 4,281,645 A | * | 8/1981 | Jobsis | 128/633 |
| 4,586,513 A | * | 5/1986 | Hamaguri | 128/633 |
| 5,566,673 A | * | 10/1996 | Shiono et al. | 128/653.1 |
| 5,678,556 A | * | 10/1997 | Maki et al. | 128/664 |
| 5,710,630 A | * | 1/1998 | Essenpreis et al. | 356/345 |
| 5,747,793 A | * | 5/1998 | Sundburg et al. | 250/227.14 |

FOREIGN PATENT DOCUMENTS

| | | |
|---|---|---|
| JP | 57-115232 | 7/1982 |
| JP | 63-275323 | 11/1988 |
| JP | 1-284758 | 11/1989 |
| JP | 3-194451 | 8/1991 |
| JP | 4-148829 | 5/1992 |
| JP | 5-126719 | 5/1993 |
| JP | 9-19408 | 1/1997 |
| JP | 9-149903 | 6/1997 |

OTHER PUBLICATIONS

Medical Physics, vol. 22, No. 12, Dec. 1995, pp. 1997–2005.
Rev. Sci. Instrument, vol. 57, No. 3, Mar. 1996, pp. 730–732.
J. Neurosurg, vol. 76, Feb. 1992, pp. 315–318.

* cited by examiner

Primary Examiner—Teresa Walberg
Assistant Examiner—Shawntina Fuqua
(74) Attorney, Agent, or Firm—Antonelli, Terry, Stout & Kraus, LLP

(57) ABSTRACT

A highly reliable optical measuring instrument for multi-channel simultaneous measurement has an intensity of light emitted from a light source modulated at different frequencies and the light is applied to multiple positions of a test object. The light which is detected from the test object is converted into electric signals by a photodiode, and modulation signals are detected by a lock-in amplifier module. The signals are processed as information on the test object interior by a processing unit. Light is applied sequentially from a light source in a preparatory measurement step prior to final measuring, and the signal level of the detection light is measured for each light applied position. A control unit controls light intensity and detection signal level to ensure that the difference in detection light levels is kept within a specified range.

24 Claims, 11 Drawing Sheets

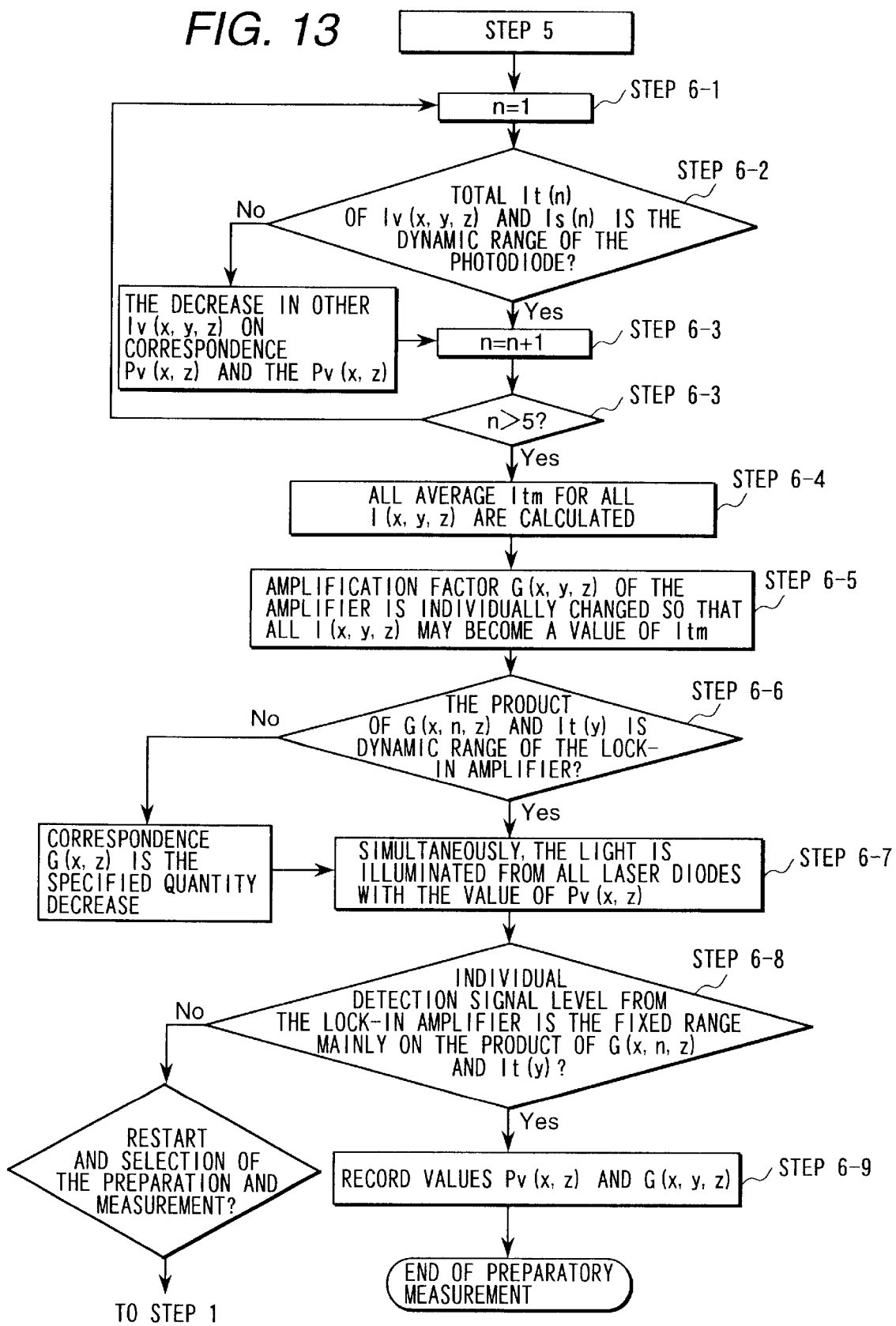

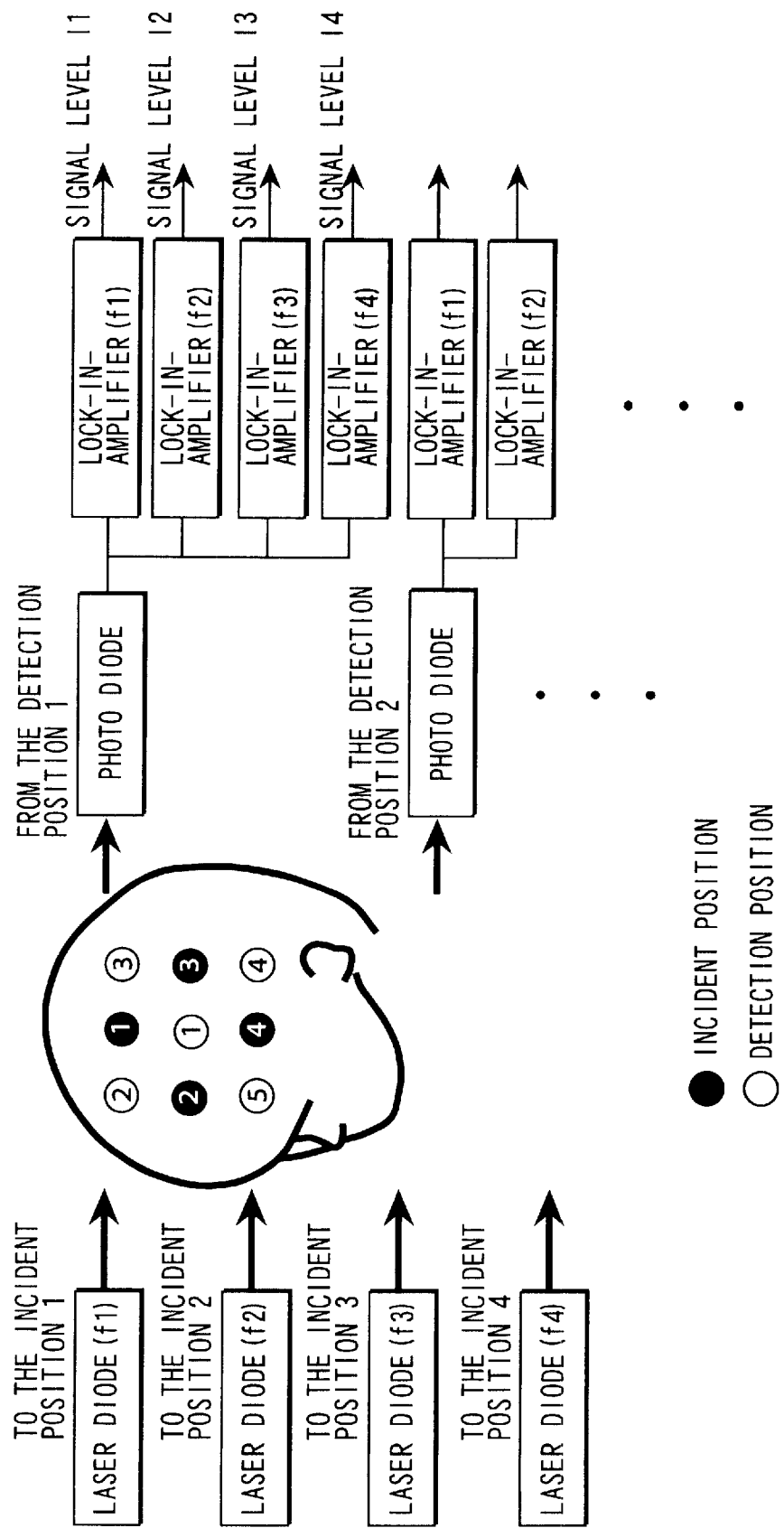

OPTICAL MEASURING INSTRUMENT

FIELD OF THE INVENTION

The present invention relates to an optical measuring instrument and especially to the optical measuring instrument suited for optical measurement of in vivo information.

BACKGROUND OF THE INVENTION

The field of clinical medicine and brain science are eagerly expecting to have a measuring instrument which allows easy measurement of in-vivo blood circulation, hemodynamics and oxygen metabolism without giving much restriction to an examinee as a test object or being hazardous to a living body. In the case of cerebral measurement, for example, specific needs for such an instrument are found in the measurement and diagnosis of cerebral diseases such as brain infarction, intracerebral bleeding and dementia as well as high order cerebral functions such as thinking, language and bodily movement. Further, such objects for measurement are not restricted to the brain alone. Such a measuring instrument is needed for preventive diagnosis of such heart diseases as heart infarction on the pectoral region and viscera diseases related to kidney and liver on the abdominal region, as well as for the measurement of oxygen metabolism in limb muscles.

For simplicity, let us restrict the object to the cerebral region alone. In the measurement and diagnosis of intracerebral diseases or high order cerebral functions, it is necessary to specify the affected site or functional region clearly. This leads of the importance of cerebral image measurement. It goes without saying that the importance of image measurement is not restricted to the cerebral region. It also applies to the pectoral and abdominal region. Examples of showing its importance can be found in the positron emission tomographic equipment (PET), functional nuclear magnetic resonance tomographic equipment (fMRI) and magnetoencephalopgraphic equipment (MEG) which are placed in extensive use as image measuring instruments for cerebral functions in recent years.

These devices have an advantage of measuring intracerebral active areas in the form of images on the one hand. On the other hand, they have an disadvantage of being large-sized and requiring complicated handling procedures. For example, installation of these devices requires large room specifically designed for their use. It goes without saying that relocation of the devices is practically impossible. Further, an examinee is confined in a device and is required to keep the same posture for a long time during the measurement. Further, the examinee has to endure severe psychological pain in addition to this heavy physical restriction. Further, such devices require special personnel assigned for maintenance and management, with the result that huge costs will be involved in the operation of the system.

By contrast, optical measurement provides an effective means to ensure easy measurement of in-vivo blood circulation, hemodynamics and oxygen metabolism without giving much restriction to examinee or being hazardous to living body. The first reason is that the blood circulation and oxygen metabolism of the living body correspond to the concentration and its change of specific pigments (hemoglobin, cytochrome, mioglobin, etc.) in the living body, and the concentration of these pigments can be obtained from the light absorbency index of the wavelength from visible to infrared ray ranges. Said blood circulation and oxygen metabolism correspond to the normal/abnormal state of the in-vivo organs and activation of the brain with respect to high order cerebral functions. The second reason to account for effective optical measurement is that the device can be the downsized and simplified by the technologies related to semiconductor laser, light emitting diode and photodiode. Further, the head need not be fixed in position during measurement by use of flexible optical fiber for measurement. This greatly reduces the restriction on the examinee and minimizes psychological pains. The third reason is that light intensity is kept within the Safety Standard (ANSIZ 136-1973, JISC6802 Standard: 2 $mW/mm^2$). Thus, the living body is not harmed by application of the light.

In addition to these advantages, optical measurement has advantages which cannot be found in said PET, MRI or MEG, for example, real time measurement, quantification of the concentration of pigment in the living body.

For example, the Japanese Patent Laid-Open NO. 115232/1982 and Japanese Patent Laid-Open NO. 275323/1988 disclose and claim a system wherein light with wave lengths from visible to infrared ray ranges is applied to the living body by effective use of the advantages of optical measurement, and in-vivo measurement is achieved by detecting the light passing through the living body by reflection therein. Further, a system of converting the living body in images by optical measurement is disclosed and claimed in the Japanese Patent Laid-Open NO. 19408/1997 and Japanese Patent Laid-Open NO. 149903/1997. The usefulness of image measurement of the living body using said light is also described, for example, in Atsushi Maki, et al. "Spatial and temporal analysis of human motor activity using noninvasive NIR topography", 1995, Medical Physics, Vol. 22, P.P. 1997 to 2005).

Generally, high time resolution and high-precision measurement are essential factors in the measurement of living bodies. In the system disclosed in said Japanese Patent Laid-Open NO. 149903/1997, a high time resolution is achieved by simultaneous measurement of multiple wavelengths required to measure the image of changes in the concentration of the living body pigment such as hemoglobin and multiple channels at multiple positions. FIG. 14 shows the over view of the system disclosed in the Japanese Patent Laid-Open NO. 149903/1997. This system allows light to be applied to multiple positions of the examinee, and detects light at the multiple positions.

In this case, the intensity of light is modulated at the frequency different for each of the positions where light is applied. For example, modulation frequencies for the light applied from light applied positions 1, 2, 3 and 4 in FIG. 14 are assumed as f1, f2, f3 and f4, respectively. Therefore, these modulation frequencies provide position information corresponding to each position where light is applied. Here the light detected at light detection position 1 includes all the modulated light. For signals output from the photodiode, however, light measurement signal on position information can be separately measured by selective measurement of each modulation frequency signal in a filter circuit of the lock-in amplifier or the like. For example, when each detection signal levels by modulation frequencies f1, f2, f3 and f4 detected by the photodiode corresponding to this light detection position 1 are assumed as I1, I2, I3 and I4, each signal is completely separated from others in the output of each lock-in amplifier synchronized at each frequency. As a result, effective simultaneous multi-channel measurement can be implemented since there is no crosstalk between measurement signals.

To get the final image from such measurement, however, a high measurement precision is required for each signal. If these detection signals contains a signal whose precision or S/N ratio is considerably low, for example, reliability of the measurement site corresponding to the signal will be reduced on the image, and this will lead to reliability of the image itself. This requires high-precision measurement with satisfactory S/N balance for all detection signals. However, the conventional devices have the following problems with respect to this measurement precision:

The state in the living body is optically uneven in normal cases. If arrangement is so made that light is to be applied to the site containing a large quantity of hemoglobins as light absorbers such as large blood vessel or light is detected at such a site, there will be attenuation of light and a considerable reduction in said detection signal level. Thus, another cause for reduction of the detection signal level in a particular measuring channel can be found in cases where there is a problem with the state of optical fiber installation, for example, where the end face of the optical fiber used for measurement is contaminated optically, or a hair is sandwiched between the optical fiber and the skin of the examinee head.

The following describes the how the S/N ratio of measurement is affected when there is an imbalance in the measurement signal level as a whole, including the detection signal with partially weak intensity as described above:

Normally, the shock noise of the light detector such as photodiode is proportional to light reaching a light detector, in other words, to the square root of the total sum of the detected light intensity. Here let us consider the case where the signal levels of I1, I2 and I3 are almost the same (I1~I2~I3), in detected signal levels I1, I2, I3 and I4 detected at the light detection position 1 in FIG. 14, and signal level I4 alone is smaller by an order of magnitude (I1>>I4). This state is assumed to occur when there is a large blood vessel close to the light applied position 4, or there is any problem installation of an optical fiber at said light applied position 4. In this case, noise due to a photodiode largely is proportional to the square root of (I1+I2+I3+I4). So level I4 which is intrinsically a signal level is heavily affected by stronger signal levels I1, I2 and I3, with the result that the S/N ratio is conspicuously reduced. To give further explanation to this point, let us take up an example where signal levels I1, I2 and I3 are further increased, with signal level I4 remaining unchanged. For level I4 in this case, noise level N will increase although the signal level, namely, S does not change.

As a result, signal S/N ratio is further deteriorated for I4. For stronger signal levels I1, I2 and I3, the S/N ratio increased. Therefore, when one optical detector is used to detect multiple optical signals, a conspicuous difference in the S/N ratio may occur between measurement channels.

In such a measurement, the following issue also occurs: In the presence of multiple strong detection signal signals, the total sum of these detection light may exceed the dynamic range due to limited dynamic range of the optical detector and lock-in amplifier and others. Said dynamic range is normally defined within the range where the linear response of the detector is ensured. However, even if the signal level has exceeded said dynamic range, a certain finite value is issued from the detector normally. But the reliability of measurement is very low for the value in this case.

As discussed above, if there is a big difference between detection signal levels, the signal S/N ratio differs greatly according to each signal. If these signals are used for imaging, image reliability will deteriorate. If these signals contain any strong detection light signal, the dynamic range of the detector will be exceeded, with the result that reliability of measurement will deteriorate.

DISCLOSURE OF THE INVENTION

The purpose of the present invention is to provide an optical measuring instrument suitable for multi-channel simultaneous measurement.

One object of the present invention is to provide an optical measuring instrument to generate multi-channel signals to characterize a test object by optical measurement of said test object;

said optical measuring instrument further characterized by comprising a measuring means to perform said measurement and a preparatory measuring means to prepare for final measurement;

wherein said preparatory measuring means further comprises a generating means to generate multi-channel signals to characterize said test object by optical measurement of said test object and an adjusting means to adjust the generated multi-channel signals so that the level differences of said signals are kept within the specified range.

Another object of the present invention is to provide an optical measuring instrument wherein light is applied to multiple positions of the test object, and the light passing through said test object is detected and measured thereby;

said optical measuring instrument further characterized by comprising a measuring means to perform said measurement and a preparatory measuring means to prepare for final measurement;

wherein said preparatory measuring means further comprises a means to apply said light sequentially to said multiple positions and a means to detect the light passing through said test object by said application of light and to generate detection signal for each of said light applied positions, thereby measuring said detection signal level.

Still another object of the present invention is to provide an optical measuring instrument characterized in that light of multiple wavelengths is applied to a test object and light passing through the test object is detected and measured;

wherein said optical measuring instrument comprises a measuring means to perform said measurement and a preparatory measuring means to prepare for final measurement;

said preparatory measuring means further comprises a means to apply said light sequentially to said test object for each of said wavelengths and a means to detect the light passing through said test object by said application of light and to generate detection signal for each of said wavelengths, thereby measuring said detection signal level.

A further object of the present invention is to provide an optical measuring instrument characterized by comprising a means to apply light of multiple wavelengths to multiple positions of test object, and a means to detect and measure the light passing through said test object by said application of light;

said optical measuring instrument further characterized in comprising a control unit to control said light intensity level and said detection signal level so that the level differences of said detection signals are kept within the specified range, when;

said light is applied sequentially to each of said positions for light application and for each of said wavelengths prior to the final measurement, the light passing through said test object by said application of light is detected and is converted into electric signals, detection signals are generated for each of said positions for light application and for each of said wavelengths based on said electric signals, and a preparatory measurement is made for said detection signal level.

BRIEF DESCRIPTION OF THE DRAWINGS

FIG. 13 is a flow chart showing the details of final adjustment (Step 6) in preparatory measurement in FIG. 7; and FIG. 14 is a general drawing showing the major points of a conventional high time resolution measuring instrument.

DESCRIPTION OF THE MOST PREFERRED EMBODIMENTS

Figure 1:
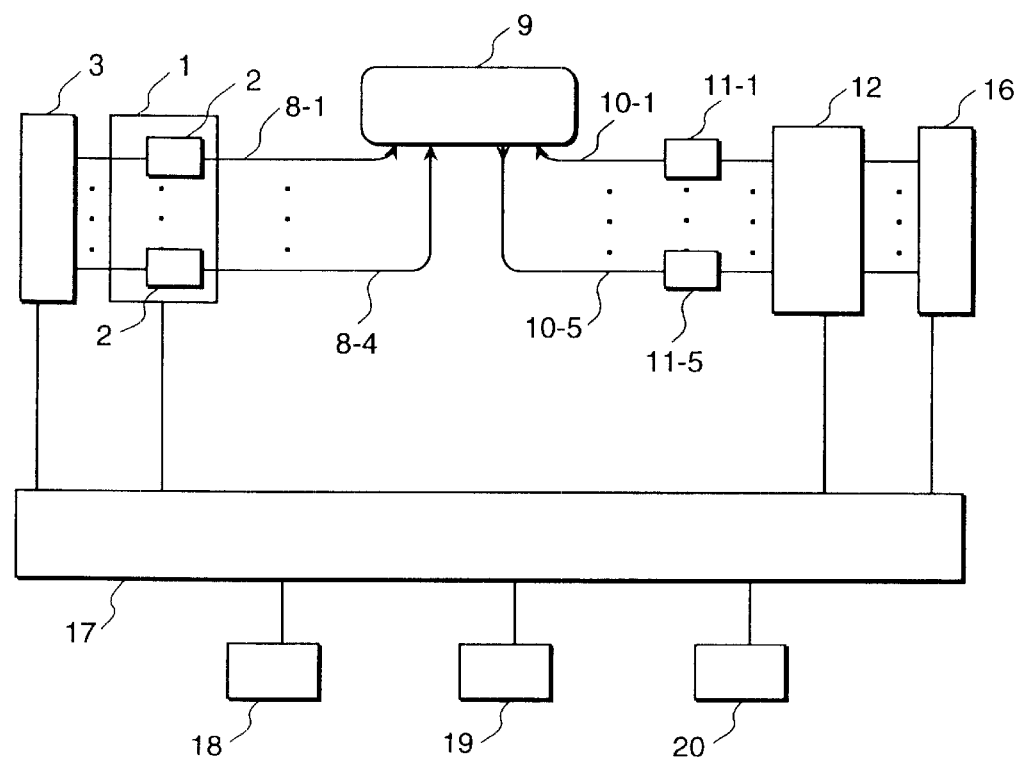
FIG. 1 is a block diagram illustrating the configuration of major components in one embodiment of an optical measuring instrument according to the present invention.

FIG. 1 is a block diagram illustrating the configuration of major components in one embodiment of an optical measuring instrument according to the present invention. In the present embodiment wherein light is applied to the test object, for example, the skin of the head, and light is reflected inside the test object thereby to detect the light passing through said test object and to image the cerebral interior, the number of measurement channels, namely the number of measurement positions are assumed as 12, and the number of signals to be measured (analog/digital conversion channels) are assumed as 24. It goes without saying that the embodiment the present invention is not restricted to the head alone. It can be extended to other sites of a living body as well as other than living body.

Light source 1 comprises four light modules 2. Each light module comprises two semiconductor lasers each emitting the light of multiple wavelengths from visible to infrared ray ranges, for example, 2 wavelengths of 780 nm and 830 nm. Values of these two wavelengths are not restricted to 780 nm and 830 nm. Further, the number of wavelengths is not limited to two. A light emitting diode may be used as this light source 1 instead of a semiconductor laser.

Each of the eight semiconductor lasers contained in this light source 1 is modulated by an oscillating unit 3 comprising eight oscillators having different oscillation frequencies.

Figure 2:
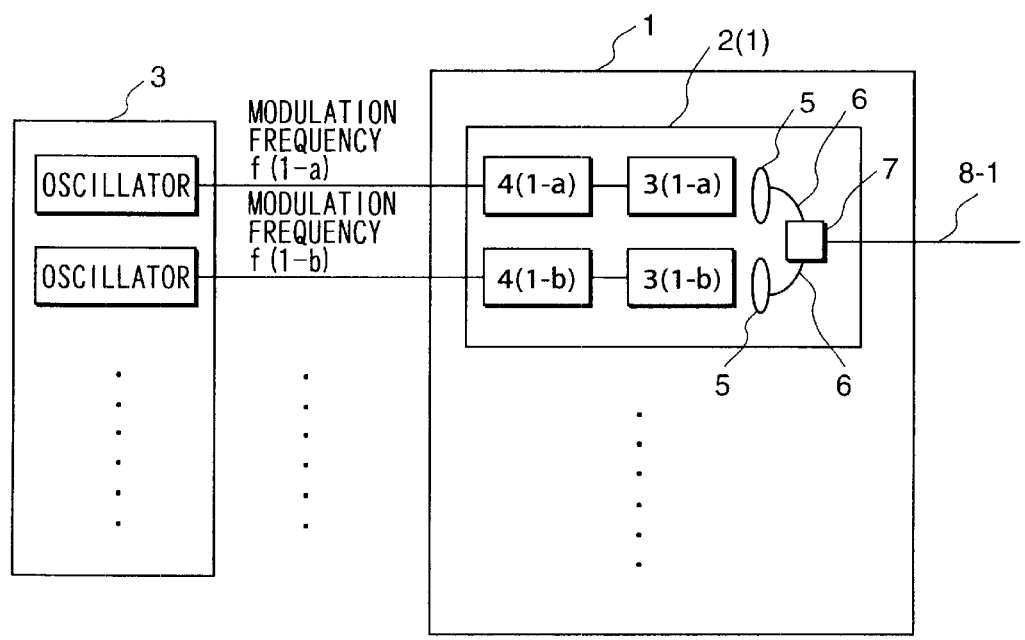
FIG. 2 is a block diagram representing the configuration inside the light module in FIG. 1.

FIG. 2 shows the configuration inside the light module 2 using an example of an light module 2(1). The light module 2(1) contains semiconductor laser 3(1-$a$), 3(1-$b$) and driving circuits 4(1-$a$) and 4(1-$b$) for these semiconductor lasers. Here numerals in parentheses indicate light module numbers, and "a" and "b" in parentheses indicate wavelengths 780 nm and 830 nm, respectively. These semiconductor laser driving circuits 4(1-$a$) and 4(1-$b$) supply d.c. bias current to semiconductor laser 3(1-$a$) and 3(1-$b$). At the same time, they also supply signals having different frequencies f(1-$a$) and f(1-$b$) by means of the oscillator 3, thereby modulating the light emitted from the semiconductor lasers 3(1-$a$) and 3(1-$b$).

This modulation is shown in the present embodiment as analog modulation by sinusoidal wave. Needless to say, it is possible to use digital modulation by rectangular wave having different time intervals, in other words, digital modulation where light is flashed at different time intervals. The light beams modulated in said manner are individually led to the optical fiber 6 by means of a condense lens 5 for each semiconductor laser. The beams of 2 wavelengths led to respective optical fibers are led into one optical fiber, e.g., the optical fiber for irradiation 8-1 for each light module by means of optical fiber coupler 7. Beams of 2 wavelengths are led into optical fibers for irradiation 8-1 to 8-4 for each light module, and are applied to four different positions for light application on the surface of test object 9 from the other ends of these irradiation optical fibers. The light reflected inside the test object 9 and passing through the test object is detected by photo diodes 11-1 to 11-5 from five light detection positions on the surface of the test object through detection optical fibers 10-1 to 10-5 arranged at said light detection positions.

The end faces of optical fibers 10-1 to 10-5 are in slight contact with the surface of the test object 9. The optical fiber is installed on the test object 9 by a probe disclosed and claimed in the Official Gazette of the Japanese Patent Laid-Open NO.149903/1997, for example.

Figure 3:
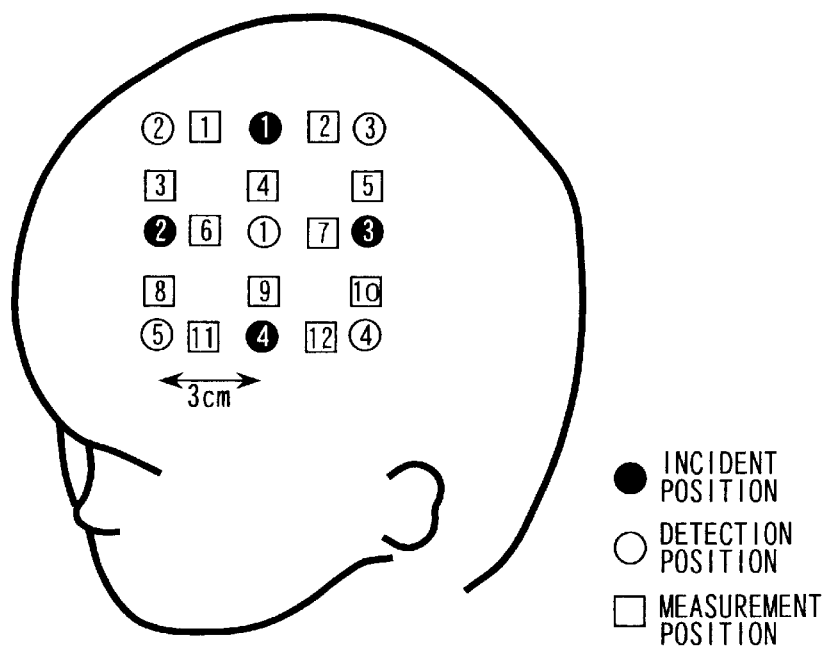
FIG. 3 is a diagram representing an example of geometric layout of light applied positions and optical detection positions on the surface of a test object in FIG. 1.

FIG. 3 shows the geometric layout of light applied positions 1 and 4, and light detection positions 1 to 5 on the surface of test object 9. In the present embodiment, light applied positions and light detection positions are alternately laid out on a tetragonal lattice. If a mid-point between adjacent light applied positions and light detection positions is the position to be measured, the number of positions to be measured, namely, the number of measurement channels is twelve, since there are a total of 12 combinations between adjacent light applied positions and light detection positions in this case. The layout of light applied positions and light detection position are disclosed, for example, in the Japanese Patent Laid-Open NO. 149903/1997 and Yuichi YAMASHITA et al. "Near-infrared topographic Measurement System: Imaging of absorbers localized in a scattering medium", 1996, Review of Scientific Instrument, Vol. 67, P.P. 730 to 732. If a space between the adjacent light applied position and detection position is set at 3 cm, light detected from each light detection position passes through the skin and cranical bone contains information on the cerebral as disclosed, for example, in P. W. McCormic et al. "Intracerebral penetration of infrared light", 1992, Journal of Neurosurgery Vol. 76, P.P. 315 to 318 (J. Neurosurg, 33, 315(1992)).

Figure 4:
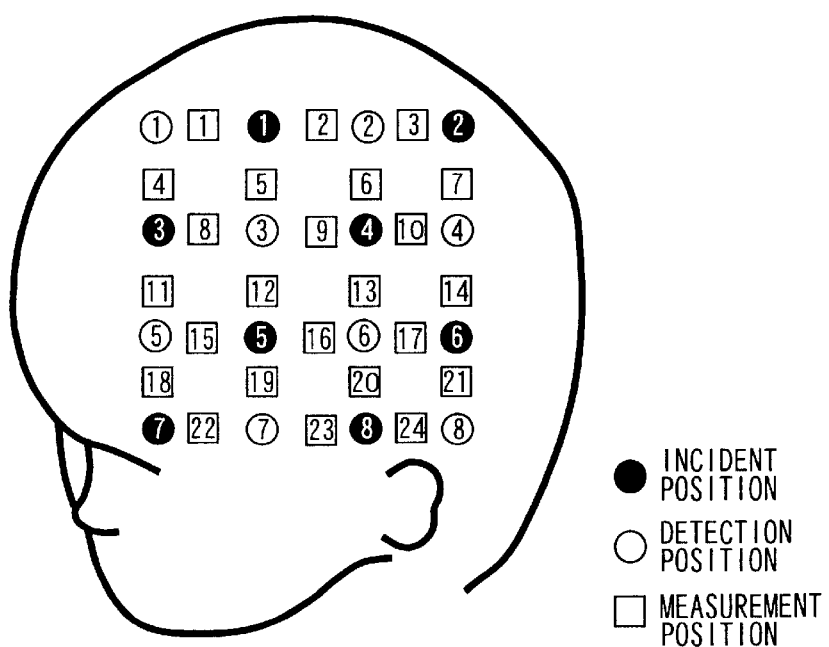
FIG. 4 is a drawing showing an layout example of light applied positions and optical detection positions in 24-channel measurement corresponding to FIG. 3.
Figure 5:
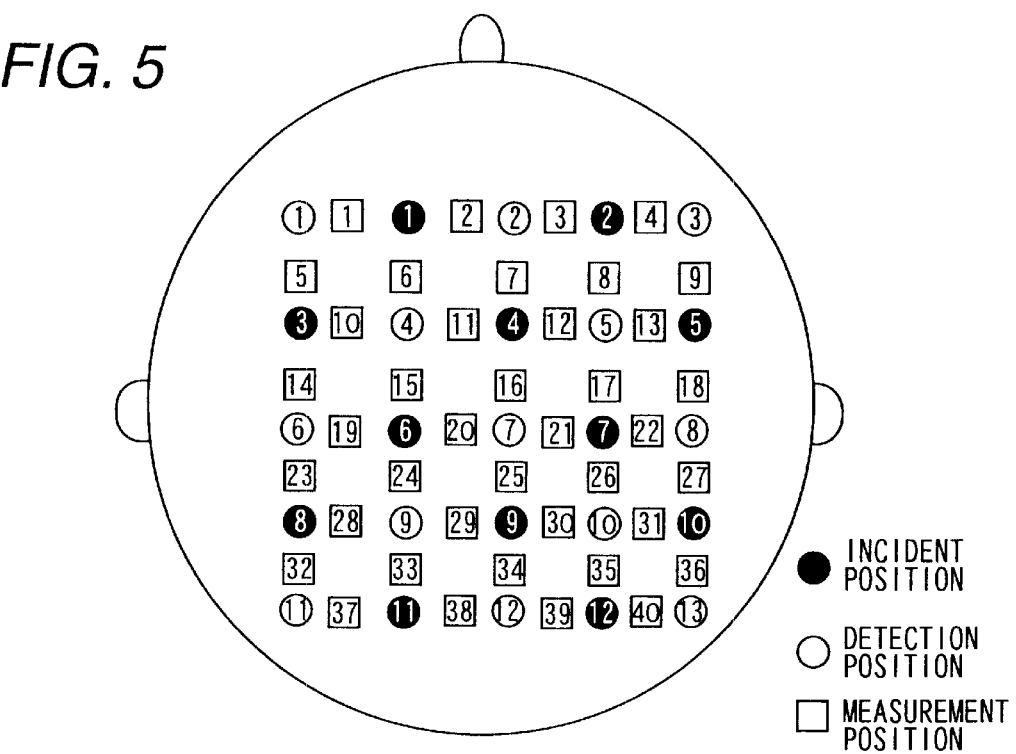
FIG. 5 is a drawing showing an layout example of light applied positions and optical detection positions in 40-channel measurement corresponding to FIG. 3.

The above description makes it clear that the cerebral in an entire range of 6 cm×6 cm can be measured if twelve measurement channels are set in said layout of the light applied position and light detection position. For simplicity, the present embodiment shows the case of twelve measurement channels. The number of measurement channels can be increased by further increasing the numbers of light applied positions and light detection positions to be laid out in a lattice form, thereby allowing easy expansion of the measurement range. For example, FIG. 4 shows the layout for light applied positions and light detection positions in the case of 24-channel measurement, and FIG. 5 shows the layout in the case of 40-channel measurement.

The space between the adjacent light applied position and detection position is not restricted to 3 cm. It can be changed according to the site of measurement.

In FIG. 1, light detected by means of each of detection optical fibers 10-1 to 10-5 is detected by five light detectors, for example, photodiodes 11-1 to 11-5 independently for each light detection position, namely, for each optical fiber for detection corresponding to each light detection position. This photodiode is preferred to be an avalanche photodiode which permits highly sensitive optical measurement. Further, a photomultiplier can be used as optical detector. After light is converted into electric signals by these photodiodes, modulated signals corresponding to the light applied position and wavelength are selectively detected by the selective detecting circuit for the modulated signals, for example, a lock-in amplifier module 12 comprising multiple lock-in amplifiers. The present embodiment shows a lock-in amplifier as a modulated signal detecting circuit designed for analog modulation. When digital modulation is used, a digital filter or digital analog signal process is used to detect modulated signals.

Figure 6:
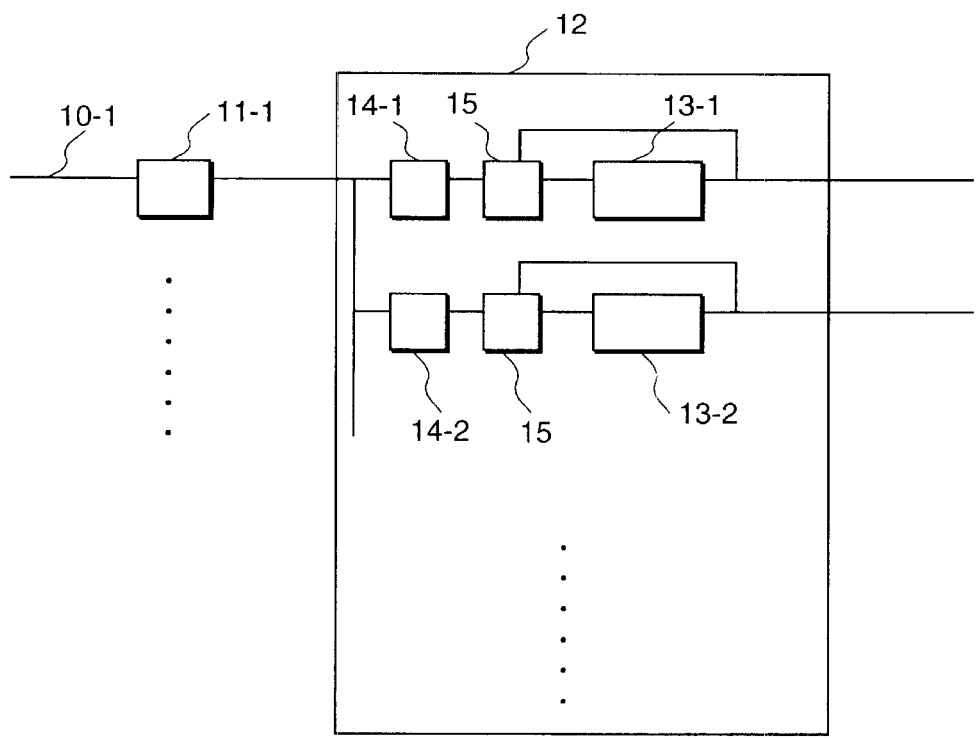
FIG. 6 is a block diagram showing the configuration of a lock-in amplifier module in FIG. 1.

FIG. 6 represents the configuration of a lock-in amplifier module 12 in FIG. 1. The following describes how modulated signals are separated, with reference to the detection signals detected through the photodiode 11-1 from the light detection position 1 in FIG. 3. From light detection position 1, it is possible to detect the light applied to adjacent light applied position 1, light applied position 2, light applied position 3 and light applied position 4. Therefore, measurement position 4, measurement position 6, measurement position 7 and measurement position 9 in FIG. 3 are the objects for measurement. Here the light detected from the light detection position 1 through the photodiode 11-1 includes eight signal components where modulation frequencies corresponding to each of beams with 2 wavelengths applied to the light applied position 1, light applied position 2, light applied position 3 and light applied position 4 are f(1-$a$), f(1-$b$), f(2-$a$), f(2-$b$), f(3-$a$), f(3-$b$), f(4-$a$) and f(4-$b$), respectively. Optical signals including these eight signal components are led into eight lock-in amplifiers 13-1 to 13-8 through eight amplifiers 14-1 to 14-8.

Eight lock-in amplifiers 13-1 to 13-8 are provided with modulation frequency signals f(1-$a$), f(1-$b$), f(2-$a$), f(2-$b$) f(3-$a$), f(3-$b$), f(4-$a$) and f(4-$b$) as reference signals. Therefore, optical signal components of 780 nm and 830 nm applied to the light applied position 1 are separated on a selective basis and are subjected to lock-in detection by means of lock-in amplifiers 13-1 and 13-2, optical signal components of 780 nm and 830 nm applied to the light applied position 2 by means of lock-in amplifiers 13-3 and 13-4, optical signal components of 780 nm and 830 nm applied to the light applied position 3 by means of lock-in amplifiers 13-5 and 13-6, and optical signal components of 780 nm and 830 nm applied to the light applied position 4 by means of lock-in amplifiers 13-7 and 13-8.

For signals detected from the light detection position 2, light detection position 3 and light detection position 4 by means of photodiodes 11-2 to 11-5 respectively, desired optical signal components are separated and subjected to lock-in detection in the similar manner. Namely, optical signals detected through photodiode 11-2 from light detection position 2 are led into four lock-in amplifiers 13-9 to 13-12 through four amplifiers 14-9 to 14-12. The optical signal component of 780 nm and 830 nm applied to the light applied position 1 and the optical signal component of 780 nm and 830 nm applied to the light applied position 2 each are separated on a selective basis and are subjected to lock-in detection. The optical signal detected from the optical detection position 3 through four amplifiers 11-3 is led to four lock-in amplifiers 13-13 to 13-16 through four amplifiers 14-13 to 4-16. The optical signal component of 780 nm and 830 nm applied to the light applied position 1 and the optical signal of 780 nm and 830 nm applied to the light applied position 3 each are subjected to lock-in detection on a selective basis. The optical signal detected from the optical detection position 4 through photodiode 11-4 is led to four lock-in amplifiers 13-14 to 13-20 through four amplifiers 14-17 to 4-20. The optical signal component of 780 nm and 830 nm applied to the light applied position 1 and the optical signal of 780 nm and 830 nm applied to the light applied position 4 each are subjected to lock-in detection. The optical signal detected from the optical detection position 5 through photodiode 11-5 is led to four lock-in amplifiers 13-21 to 13-24 through four amplifiers 14-21 to 4-24. The optical signal component of 780 nm and 830 nm applied to the light applied position 2 and the optical signal of 780 nm and 830 nm applied to the light applied position 4 each are subjected to lock-in detection on a selective basis.

As can be seen from FIG. 3, when light detection position 2, light detection position 3, light detection position 4, or light detection position 5 is the position where light is to be detected, the position to be measured is the measurement position 1, measurement position 3, measurement position 2, measurement position 5, measurement position 10, measurement position 12, measurement position 8 or measurement position 11.

As described above, when there are two wavelengths and twelve measurement positions, the number of signals to be measured (number of analog/digital conversion channels) is 24. So the lock-in amplifier module 12 contains a total of 24 lock-in amplifiers 13-1 to 13-24 for these channels. Each of the analog output signals of these lock-in amplifiers 13-1 and 13-24 characterizes the test object 9, and is converted into a digital signal by the AD converter 16. These measurements are controlled by a control unit 17. Further, measured signals are recorded by a recording unit 18. Using the amount of detection light of two wavelengths for each measurement position, these recorded signals are processed at the processor 19 to calculate the changes in oxygenated hemoglobin concentration accompanying the cerebral activities, changes in deoxygenated hemoglobin concentration and changes in the entire hemoglobin concentration as a total of these hemoglobin concentrations, for example, according to the method disclosed in the Japanese Patent Laid-Open NO.19408/1997 and said Atsushi Maki, et al. "Spatial and temporal analysis of human motor activity using noninvasive NIR topography", 1995, Medical Physics, Vol. 22, P.P. 1997 to 2005). The result of calculation is are converted in an image and is shown as a topographic image on the display unit 20, for example.

Figure 7:
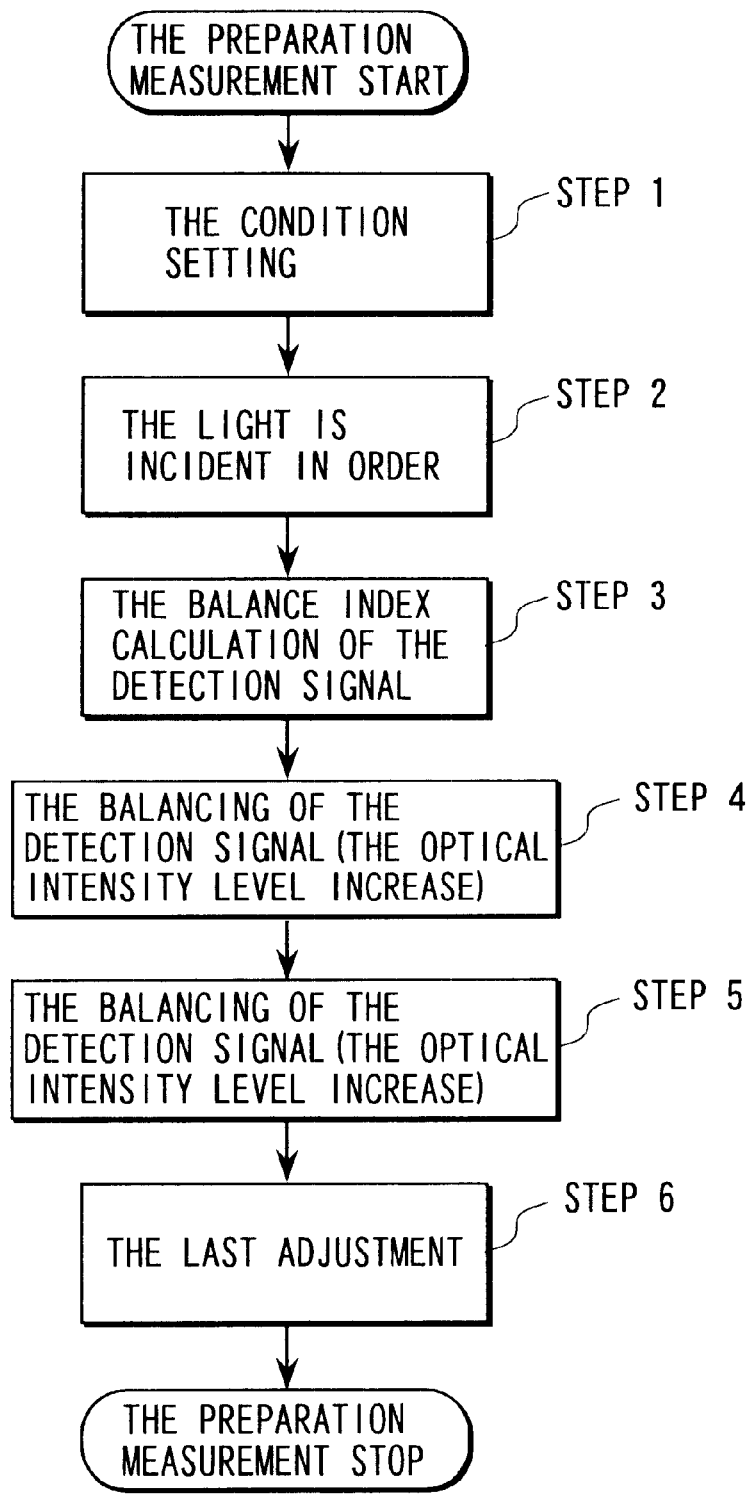
FIG. 7 is a flow chart representing the overview of the entire preparatory measurement in an embodiment according to the present invention.

Here full-scale measurement of changes in concentration of hemoglobin or the like, namely, preparatory measurement prior to final measuring is carried out. FIG. 7 shows the flow chart representing the overview of this preparatory measurement. The following describes the details of each processing in FIG. 7:

(Step 1: Configuration Setting)

Figure 8:
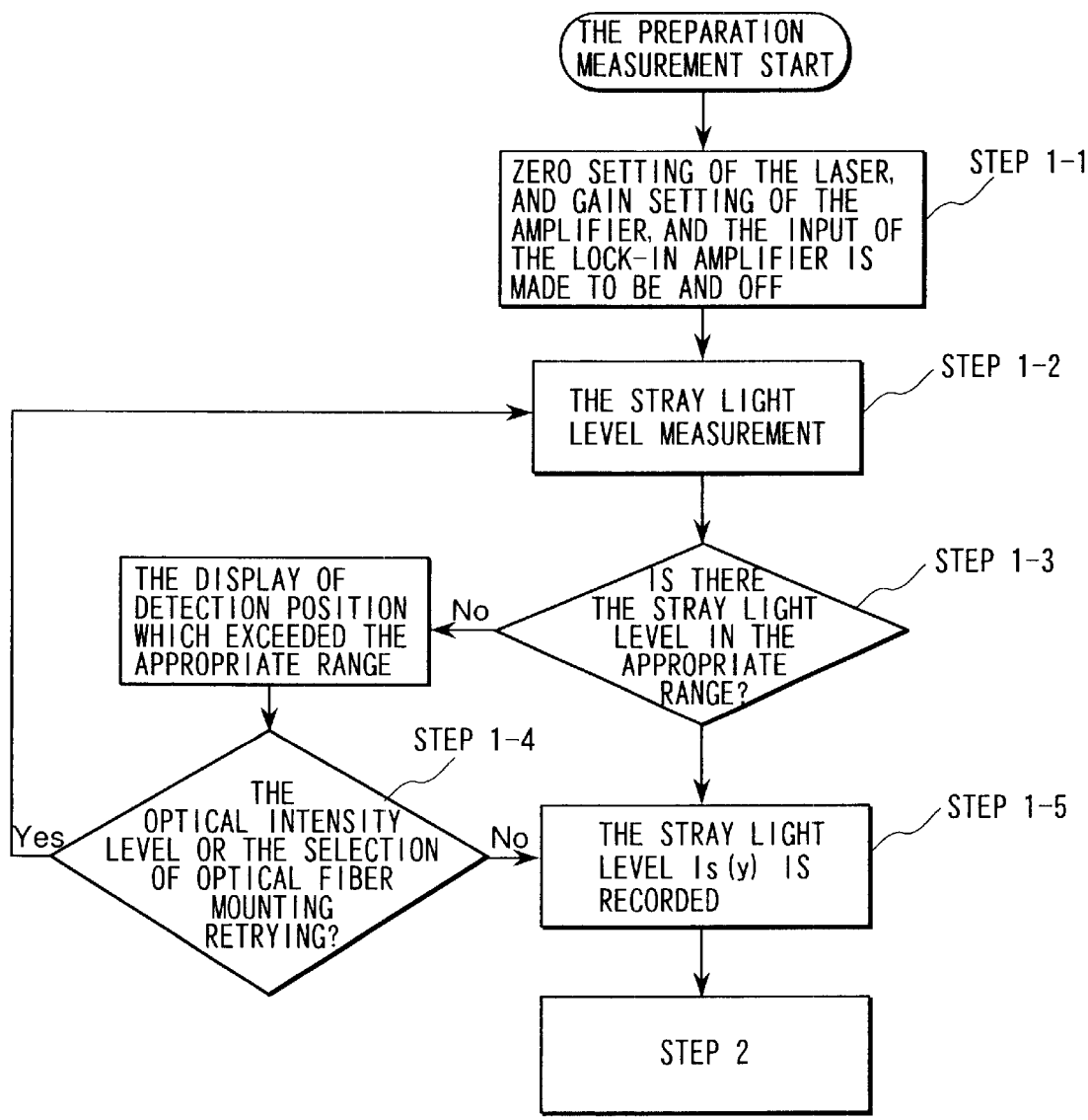
FIG. 8 is a flow chart showing the details of the configuration setting processing (Step 1) in preparatory measurement in FIG. 7.
Figure 9:
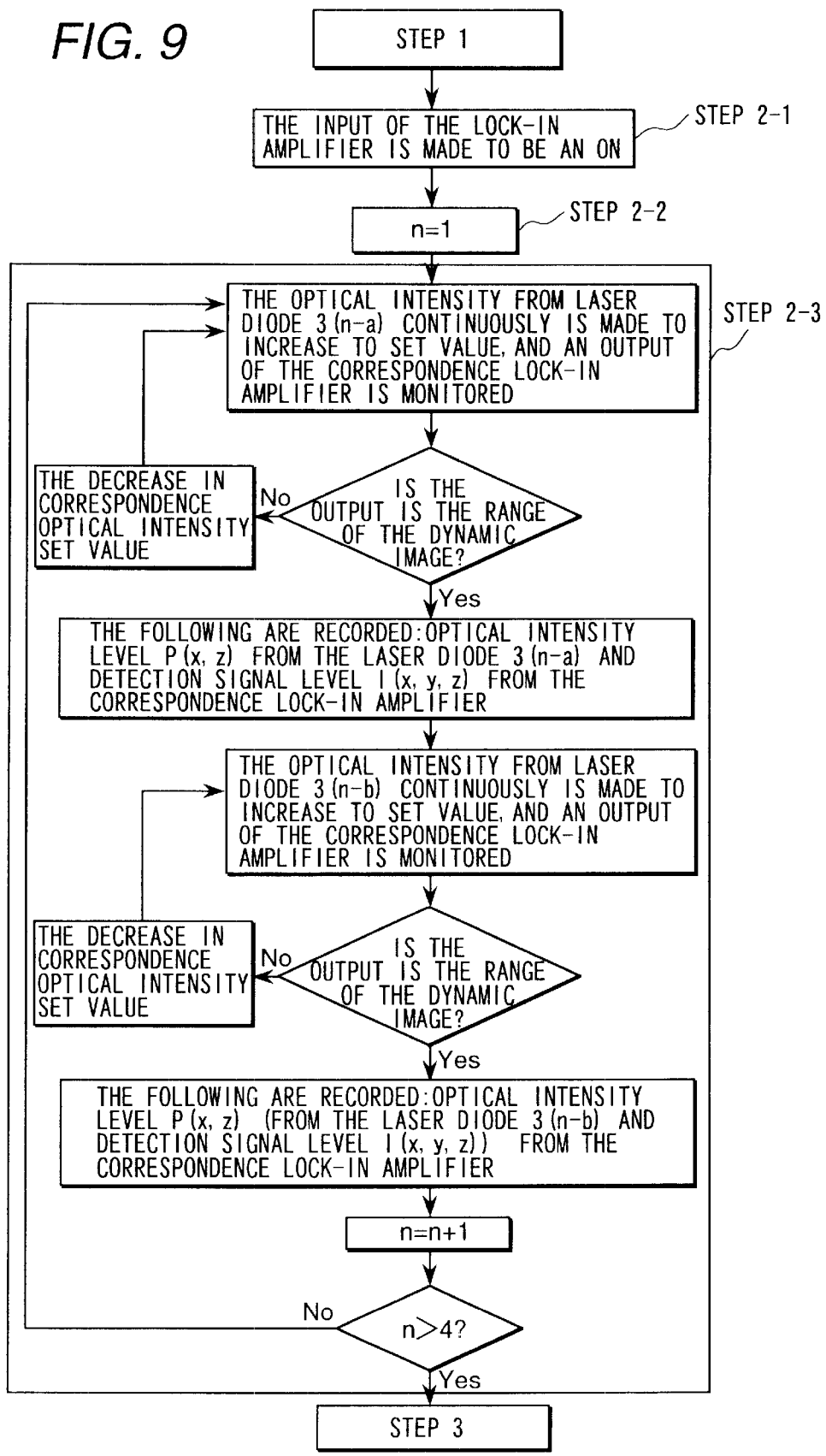
FIG. 9 is a flow chart showing the details of the optical sequential application (Step 2) in preparatory measurement in FIG. 7.

The following describes the details of processing in Configuration setting (Step 1) in FIG. 7 with reference to the flow chart in FIG. 8.

(Step 1-1)

The driving circuit 4 of light source 1 is controlled by a control unit 17 to set the optical output of all the semiconductor lasers to zero level. At the same time, the increase rate or gain of the amplifier 14 in the lock-in amplifier module 12 is set to a certain value, for example, "1". Each switch 15 on the back of the amplifier is turned off, so that signals from the amplifier 14 will enter the AD converter 16 directly, without entering each lock-in amplifier.

(Step 1-2)

When the optical outputs from all the semiconductor lasers are zero, calculation is made assuming that the d.c. output from each photodiode is on the stray light level.

(Step 1-3)

If stray light level in each photodiode exceeds a specified range, light detection position corresponding to said photodiode is displayed on the display unit 20.

(Step 1-4)

The operator is prompted to review the illumination level in the measurement chamber and installation of the optical fiber. If the operator selects the review mode, go back to step 1-2. If the review is not selected, go to Step 1-5.

(Step 1-5)

Assume that the variable showing the light detection position is "y", and the stray light level value corresponding to each photodiode 11-y is "Is(y)". They are recorded in recording unit 18.

(Step 2: Sequential Application of Light)

Figure 10:
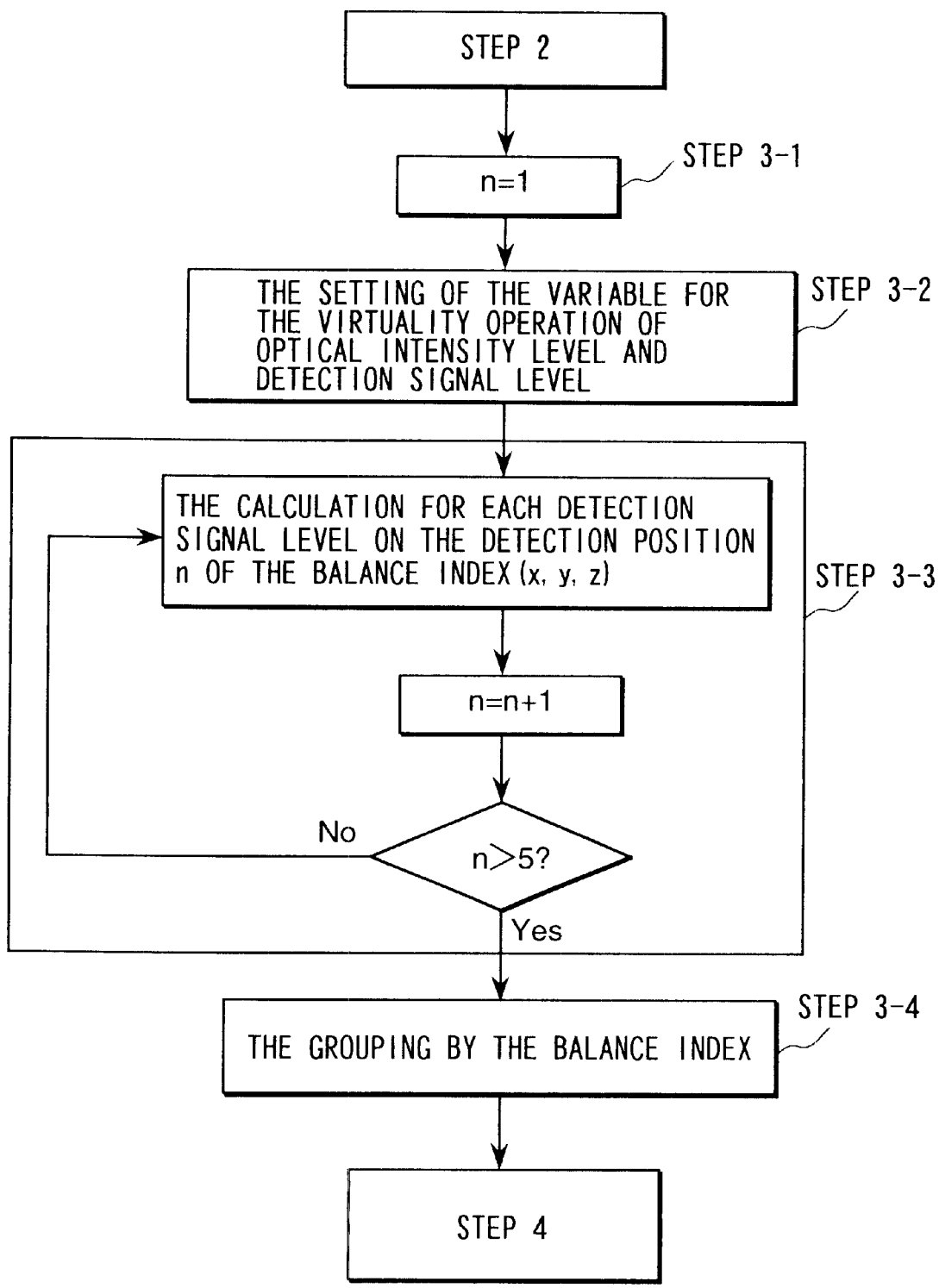
FIG. 10 is a flow chart showing the details of detection signal balance indicator calculation (Step 3) in preparatory measurement in FIG. 7.

The following describes the details of processing of sequential application of light in FIG. 7 (Step 2) with reference to the flow chart in FIG. 10.

(Step 2-1)

Turn on each switch 15 in the lock-in amplifier module 12 so that output signals from the amplifier 14 will enter each lock-in amplifier.

(Step 2-2)

Substitute 1 into variable n.

(Step 2-3)

The driving circuit 4(1-$a$) and oscillator 3 related to semiconductor laser 3(1-$a$) having a wavelength of 780 nm to be applied to light applied position 1 in FIG. 3 is controlled at the light applied position n where n=1 in this case, and the optical output from said semiconductor laser is increased continuously or discreetly from zero level to a certain set value. Here measurement is also made of the detection signal in said lock-in amplifier connected to photodiodes 11-1 and 11-3 to each of adjacent detection positions 1, 2 and 3 adjacent to light applied position 1 and synchronized at the same frequency as modulation frequency f(1-$a$) of the semiconductor laser 3(1-$a$). In this case, confirmation is made to ensure that all reactions of lock-in amplifier detection signal level with respect to changes in the optical output level of the light source are kept within the range of linear reactions of photodiode and lock-in amplifier, namely, within the dynamic range. Here if any one of the detection signal levels is not linear in excess of this dynamic range, the optical output set value from the semiconductor laser 3(1-$a$) is reduced to a specified value and the same procedure is repeated. In this case, both the light intensity level of the semiconductor laser and detection signal level from each lock-in amplifier are recorded. For example, assume that a variable showing the light applied position is x, a variable showing the light detection position is y, a variable in the form of letter showing the wavelength is z, the light intensity level is P(x, z), and detection signal level is I(x, y, z). "z" will be replaced by letter a for the wavelength of 780 nm and by letter v for the wavelength of 830 nm.

After that, the optical output of this semiconductor laser is set to zero.

When position n=1 in this case, the same step as that for the case of wavelength of 780 nm is repeated for the semiconductor laser 3(1-$b$) having a wavelength of 830 nm to be applied to the light applied position 1.

Then 1 is added to n. If n is the number of the light applied positions, namely, 4 or less, the same step is sequentially repeated with respect to semiconductor laser 3(n-$b$) and 3 (n-$b$).

(Step 3: Calculation of Detection Signal Balance Indicator)

The following describes the details of calculation of detection signal balance indicator in FIG. 7 (Step 3) with reference to the flow chart given in FIG. 10.

(Step 3-1)

Substitute numeral 1 into variable n.

(Step 3-2)

The light intensity level P(x, z) and detection signal level I(x, y, z) introduced in Step 2-3 are used as initial conditions, and Pv(x, z) and Iv(x, y, z) are set as their virtual operation variable.

(Step 3-3)

For photodiode 11-n corresponding to detection position n where n=1, for example, the average value of detection signal levels Iv(1, 1, a), Iv(1, 1, b), Iv(2, 1, a), Iv(2, 1, b), Iv(3, 1, a), Iv(3, 1, b), Iv(4, 1, a), Iv(4, 1, b) other than the stray light detected by the photodiode 11-1 is set at Im(n), namely, Im(1). The ratio of each detection signal level with respect to this average value is calculated as balance indicator. This balance indicator is indicated as V(x, y, z), using three variables; light applied position x, detection position y and wavelength z. For example, balance indicator V(1, 1, a) for detection signal level Iv(1, 1, a) is Iv(1, 1, a)/Im(1).

This indicator means that the relevant signal level is average if V(x, y, z) has a value 1. If it exceeds 1, the signal level tends to be strong. If it is below 1, the signal level tends to be weak. If all the balance indicators are 1 for all the signals from the photodiode, it indicates a well balanced detection level. If the value exceeding 1 or close to zero is mixed, the detection signal level is heavily unbalanced, Add "1" to "n". If n is equal to or less than the number of detection positions, namely, n is 5 or less, the same step is applied to photodiode 11-n for detection position n, and the balance indicator is calculated for all signal levels.

(Step 3-4)

All balance indicators V(x, y, z) calculated in Step 3-3 are grouped according to their values. For example, Group A means that V(x, y, z) is 1.5 or more, and Group B denotes that it is in the range from 1.5 to 0.5. Group C indicates that it is in the range from 0.5 to 0.2, and group D shows that it is 0.2 or less. Imbalance of detection signal level often occurs with respect to a specific light applied position or light detection position including measurement site or optical fiber installation. Hence, Groups C and D contain the members which have the same optical fiber. These light applied position and light detection position are obtained and, at the same time, light applied position and light detection position pertaining to group A are extracted.

(Step 4: Balancing the Detection Signal (Increase of Light Intensity Level))

Figure 11:
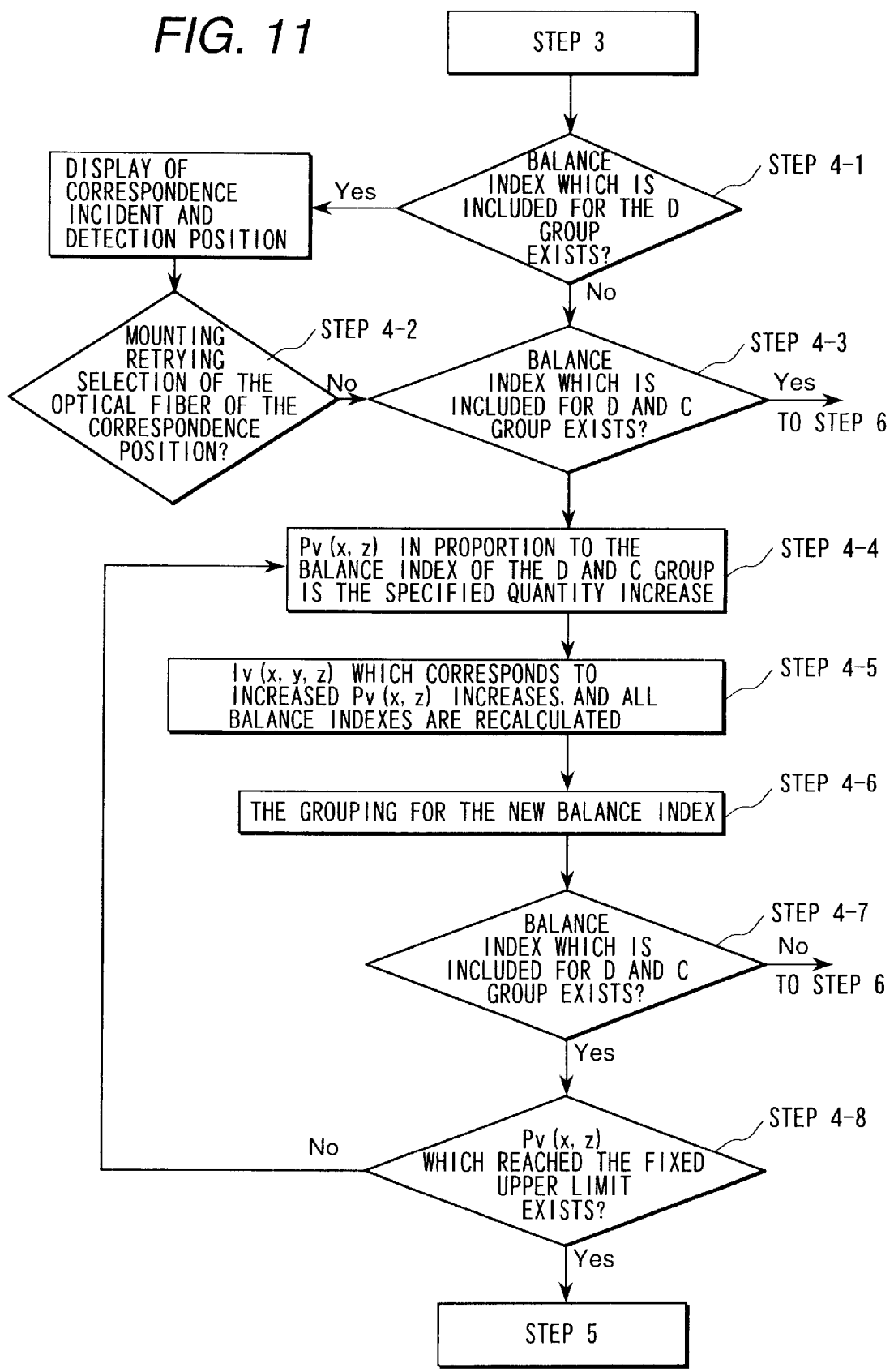
FIG. 11 is a flow chart showing the details of detection signal balancing (increase of light intensity level) (Step 4) in preparatory measurement in FIG. 7.

The following describes the details of balancing of detection signal balance in FIG. 7 (increase of light intensity level) (Step 4) with reference to the flow chart in FIG. 11:

(Step 4-1)

When V(x, y, z) classified as Group D in the grouping of the balance indicators is included, the relevant light applied position and light detection position including the wavelength are indicated on the display unit 20.

(Step 4-2)

The operator is prompted to review reinstallation of optical fiber in the relevant light applied position and light detection position. If the operator selects review, go back to step 1. If not, go to Step 4-3.

(Step 4-3)

When V(x, y, z) classified as Groups D and C in the grouping of the balance indicators is not included, go to Step 6.

(Step 4-4)

Light intensity level Pv(x, z) for virtual operation from the light applied position corresponding to the balance indicator of Groups D and C is increased by a specified width, and the increased value is replaced by Pv(x, z).

(Step 4-5)

All the relevant detection signal levels Iv(x, y, z) for virtual operation related to the light applied position of the Pv(x, z) increased in Step 4-4 are replaced by the value proportional to the increase rate of Pv(x, z) respectively. Recalculation is made for all V(x, y, z), and values are replaced by new ones.

(Step 4-6)

Grouping is performed again for a new balance indicator.

(Step 4-7)

When the relevant V(x, y, z) belonging to Groups C and D is not included, go to Step 6.

(Step 4-8)

If there is a Pv(x, z) having reached the specified upper limit value, go to Step 5. If not, go back to Step 4-4, and repeat the same procedure.

(Step 5: Balancing of Detection Signal (Decrease of Light Intensity Level)

Figure 12:
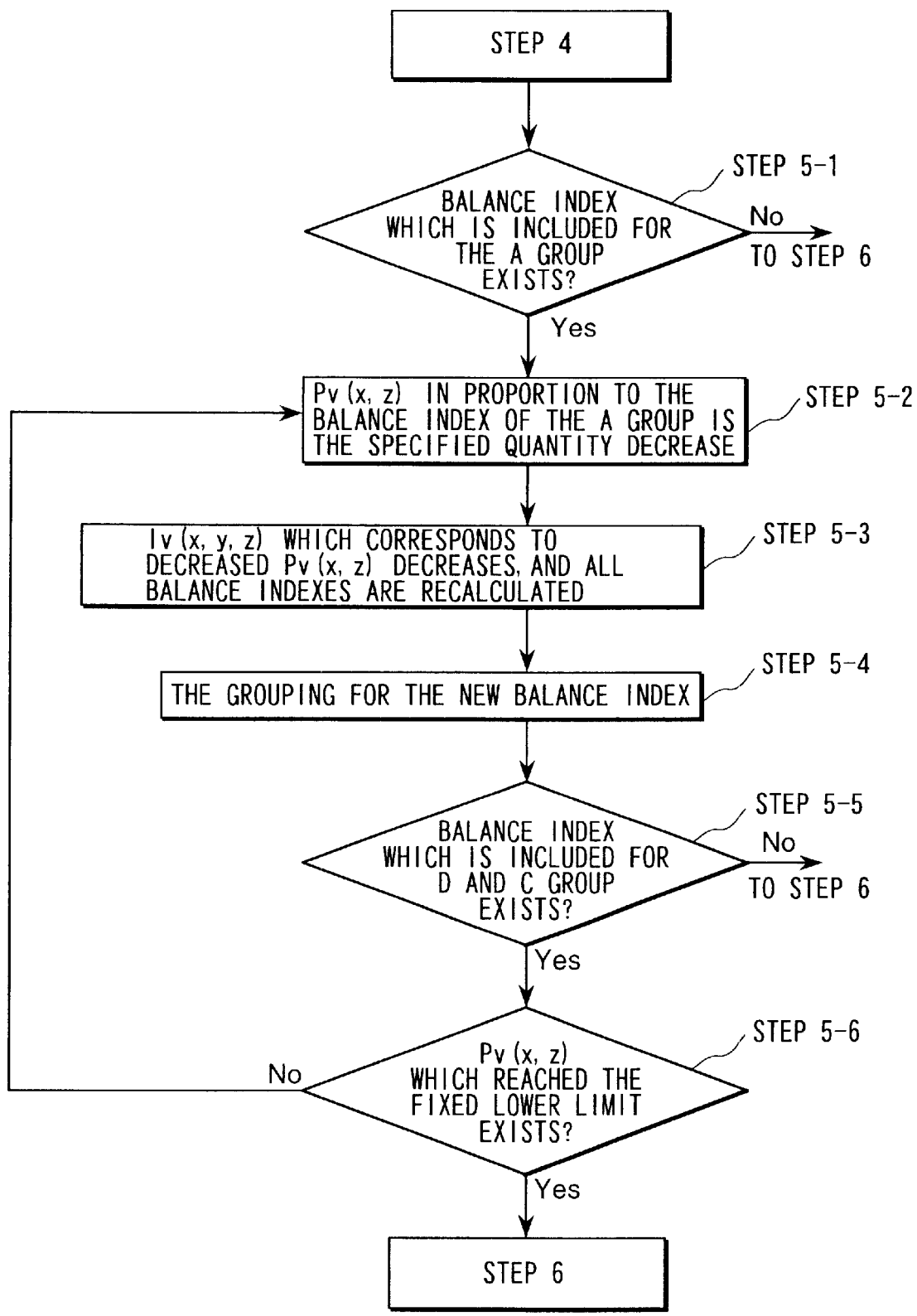
FIG. 12 is a flow chart showing the details of detection signal balancing (decreased of light intensity level) (Step 5) in preparatory measurement in FIG. 7.

The following describes the details of balancing of detection signal (decrease of light intensity level) (Step 5) in FIG. 7 with reference to flow chart in FIG. 12.

(Step 5-1)

When V(x, y, z) classified as Group A in the grouping of the balance indicators is not included, go to Step 6.

(Step 5-2)

Light intensity level Pv(x, z) for virtual operation from the light applied position corresponding to the balance indicator of Group A is decreased by a specified width, and the decreased value is replaced by Pv(x, z).

(Step 5-3)

All the relevant detection signal levels Iv(x, y, z) for virtual operation related to the light applied position of the Pv(x, z) decreased in Step 5-2 are replaced by the value proportional to the decrease rate of Pv(x, z) respectively. Recalculation is made for all V(x, y, z), and values are replaced by new ones.

(Step 5-4)

Grouping is performed again for a new balance indicator.

(Step 5-5)

When the relevant V(x, z) belonging to Group C and D is not included, go to Step 6.

(Step 5-6)

If there is a Pv(x, z) having reached the specified lower limit value, go to Step 6. If not, go back to Step 5-1, and repeat the same procedure.

(Step 6: Final adjustment)

The following describes the details of final adjustment (Step 6) in FIG. 7 with reference to flow chart in FIG. 13.

(Step 6-1)

Substitute numeral 1 into variable n.

(Step 6-2)

Assume that the stray light level detected by the photodiode 11-n corresponding to detection position n where n=1, for example, is Is(1), and the total sum of Is(1) and detection signal levels Iv(1, 1, a), Iv(1, 1, b), Iv(2, 1, a), Iv(2, 1, b), Iv(3, 1, a), Iv(3, 1, b), Iv(4, 1, a), Iv(4, 1, b) is It(y). In other words, It(1) is assumed when the detection position n is 1. When the value of this total sum exceeds the dynamic range of the photodiode, the detection signal level Iv(x, y, z) is subtracted by a uniform ratio so that It(1) is the upper limit value of this dynamic range. At the same time, the Pv(x, z) related to the subtracted Iv(x, y, z) and other Iv(x, y, z) related to the Pv(x, z) are also subtracted by the same ratio.

(Step 6-3)

Then add "1" to "n". If n is equal to or less than the number of detection positions, namely, n is 5 or less, the same procedure is sequentially repeated for detection position n.

(Step 6-4)

Calculate the average Itm for all variables Iv(x, y, z) for virtual operation.

(Step 6-5)

Change the amplification factors of the individual amplifiers 14 in the lock-in amplifier module 12 independently so that all detection signal levels of Iv(x, y, z) will be Itm, where the amplification factor of the amplifier related to individual Iv(x, y, z) is assumed as G(x, y, z).

(Step 6-6)

If the product between the It(y) input into the individual lock-in amplifiers and G(x, y, z) exceeds the dynamic range of the lock-in amplifier, subtract G(x, y, z) related to the relevant lock-in amplifier so that the product between It(y) and G(x, y, z) will be the upper limit value of this dynamic range.

(Step 6-7)

Light is simultaneously applied from all the semiconductor lasers at light source 1 in conformity to the value of Pv(x, z) in each light applied position at each wavelength in the phase of this Step.

(Step 6-8)

If each actual detection signal level from each lock-in amplifier is not kept within the specified range around the product between Iv(x, y, z) and G(x, y, z), this is reported to the operator. In this case, if the operator selects re-execution of preparatory measurement, go back to step 1.

(Step 6-9)

Values Pv(x, z) and G(x, y, z) are recorded in the recording unit 18. The process of preparatory measurement is now complete. This is followed by the process of final measurement using the values Pv(x, z) and G(x, y, z). In the preparatory measurement discussed above, light intensity level of each semiconductor laser is changed by d. c. current or modulated current from the oscillator and driving circuit 4 being controlled by the control unit 17. Further, changes in said light intensity level are not restricted to the changes of applied current. Said change can be accomplished by introducing a variable light damping filter in the optical path from the semiconductor laser to the test object.

The present embodiment is not restricted to the flow of the preparatory measurement shown in the above embodiment.

INDUSTRIAL FIELD OF APPLICATION

The present invention provides a highly reliable optical measuring instrument suitable for multi-channel simultaneous measurement.

What is claimed is:

1. An optical measuring instrument wherein light is applied to multiple positions of the test object, and the light passing through said test object is detected and measured thereby;

said optical measuring instrument further characterized by comprising a measuring means to perform said measurement and a preparatory measuring means to prepare for final measurement;

where in said preparatory measuring means further comprises a means to apply said light sequentially to said multiple positions and a means to detect the light passing through said test object by said application of light and to generate detection signal for each of said light applied positions, thereby measuring said detection signal level.

2. An optical measuring instrument wherein light is applied to multiple positions of the test object, and the light including multiple signal components passing through said test object is detected and measured thereby;

said optical measuring instrument further characterized by comprising a measuring means to perform said measurement and a preparatory measuring means to prepare for final measurement;

wherein said preparatory measuring means further comprises a means to apply said light including multiple signal components sequentially to said multiple positions and a means to detect the light passing through said test object by said application of light and to generate detection signal for each of said light applied positions and for each of said signal components, thereby measuring said detection signal level.

3. An optical measuring instrument wherein light of multiple wavelengths is applied to multiple positions of the test object, and the light passing through said test object is detected and measured thereby;

said optical measuring instrument further characterized by comprising a measuring means to perform said measurement and a preparatory measuring means to prepare for final measurement;

wherein said preparatory measuring means further comprises a means to apply said light sequentially for each of said light applied positions and for each of said wavelengths, a means to detect the light passing through said test object by said application of light and to convert them into electric signals, and a means to generate detection signals for each of said positions for light application and for each of said wavelengths based on said electric signals, thereby measuring said detection signal level.

4. An optical measuring instrument according to any one of claims 1, 2 and 3 further characterized in that said preparatory measurement means comprises a means to detect stray light when said light is not applied to said test object and to generate stray light signals, thereby measuring said stray light signal level.

5. An optical measuring instrument according to claim 4 characterized in that said preparatory measurement means comprises a means to increase the intensity of said applied light from the zero level to a specified level of intensity.

6. An optical measuring instrument according to claim 5 characterized in that said preparatory measurement means comprises a means to decrease said applied light intensity level to a specified intensity level if the reaction of said detection signal level when the intensity of said applied light is increased is non-linear.

7. An optical measuring instrument according to claim 3 wherein said final measuring means is characterized in that said light of multiple wavelengths is applied simultaneously to said multiple light applied positions.

8. An optical measuring instrument according to claim 3 wherein said final measuring means is characterized by comprising a means to apply said light of multiple wavelengths simultaneously to said multiple positions and a means to detect the light passing through said test object by said application of light and to generate detection signal for each of said light applied positions and for each of said wavelengths;

wherein said final measuring means and said preparatory measurement means are further characterized in that the light passing through said test object is detected from multiple light detection positions of said test object.

9. An optical measuring instrument according to claim 8 wherein each of said final measuring means and said preparatory measurement means comprises a means to give different modulation to said applied light for each of said light applied positions and for each of said wavelengths, and generates detection signals for each of said light applied positions and for each of said wavelengths using a modulation detector.

10. An optical measuring instrument according to claim 9 further characterized in that said different modulation is given by an analog method using different frequency signals.

11. An optical measuring instrument according to claim 9 further characterized in that said different modulation is given by a digital method wherein light applied for each of said wavelengths and for each said light applied positions is flashed at different time intervals.

12. An optical measuring instrument according to any one of claims 9 to 11 further characterized in that each of said final measuring means and preparatory measuring means comprises a means to amplify said electric signal led into said modulation detector independently by means of each amplifier.

13. An optical measuring instrument according to any one of claims 9 to 11 further characterized in that said preparatory measurement means comprises a means to allow independent change in the intensity level of the light modulated for each said wavelength and for each said light applied position.

14. An optical measuring instrument according to any one of claims 9 to 11 further characterized in that said preparatory measurement means comprises a means to change the increase rate of said amplifier or the intensity level of said applied light so that the difference among said detection signal levels is kept within the specified range.

15. An optical measuring instrument according to any one of claims 9 to 11 further characterized in that said preparatory measurement means comprises a means to detect stray light when said light is not applied to said test object and to generate stray signal, and a means to change the following sums so that the total sum between the sum of said detection light levels for said light detection positions and the sum of said stray light signal levels is kept within the specified range.

16. An optical measuring instrument according to claim 15 further characterized in that said preparatory measurement means comprises a means to calculate the average of said detection light levels for all said light detection positions and to change the amplification factor of said amplifier so that each of said detection light levels will be virtually the same as said average value.

17. An optical measuring instrument according to claim 16 further characterized in that said preparatory measurement means comprises a means to determine if the product between said total sum and said amplification factor of the amplifier is kept within the specified range.

18. An optical measuring instrument according to claim 17 further characterized in that said preparatory measurement means comprises a means to record said applied light intensity level and said amplification factor of amplifier when the product between said total sum and said amplification factor of amplifier is kept within the specified range.

19. An optical measuring instrument according to claim 17 further characterized in that said preparatory measurement is performed again if the product between said total sum and said amplification factor of the amplifier is not kept within the specified range.

20. An optical measuring instrument according to claim 18 further characterized in that said final measurement is performed when said recorded light intensity level and amplification factor are maintained.

21. An optical measuring instrument according to any one of claims 8 to 11 further characterized by comprising a means to calculate a balance indicator on said detection signal and to indicate the corresponding wavelength, light applied position and light detection position if said balance indicator has failed to reach the specified level.

22. An optical measuring instrument characterized by comprising a means to apply light of multiple wavelengths to multiple positions of test object, and a means to detect and measure the light passing through said test object by said application of light;

said optical measuring instrument further characterized in that said light is applied sequentially to each of said positions for light application and for each of said wavelengths prior to the final measurement, the light passing through said test object by said application of light is detected and is converted into electric signals, detection signals are generated for each of said positions for light application and for each of said wavelengths based on said electric signals, and a control unit is incorporated to control said light intensity level and said detection signal level so that the level differences of said detection signals are kept within the specified range.

23. An optical measuring instrument according to claim 22 further characterized in that said light applying means includes a light emitting diode or semiconductor laser for each of said light applied positions and for each of said wavelengths, and changes said light intensity level by adjusting the d. c. current or modulation current applied to said light emitting diode or semiconductor laser.

24. An optical measuring instrument according to claim 22 further characterized in that said light applying means comprises a dimming filter to change the intensity level of the light emitted therefrom for each of said light emitting diode or semiconductor laser.

* * * * *